United States Patent [19]

Kaufman et al.

[11] Patent Number: 4,927,214
[45] Date of Patent: May 22, 1990

[54] OPERATING ROOM INSTRUMENT TABLE

[76] Inventors: Howard H. Kaufman, 11 Heather Dr., Morgantown, W. Va. 26505; German Nunez, 14713 SW. 110 Ter., Miami, Fla. 33196

[21] Appl. No.: 208,074

[22] Filed: Jun. 17, 1988

[51] Int. Cl.⁵ .............................................. A47B 77/00
[52] U.S. Cl. ..................... 312/195; 312/223; 312/234.1; 108/159
[58] Field of Search ............ 312/107, 195, 196, 245, 312/246, 209, 279, 234.1, 234.2, 234.3, 234.4, DIG. 33, 223; 248/349; 108/26, 66, 64, 154, 157, 159, 94

[56] References Cited

U.S. PATENT DOCUMENTS

| 1,754,094 | 4/1930 | Glass, Sr. ......................... 248/349 X |
| 2,215,462 | 9/1940 | Davidson Jr., et al. .......... 108/66 X |
| 2,575,661 | 11/1951 | Hickey ............................. 312/209 X |
| 3,080,835 | 3/1963 | Guglielmi ........................ 108/147 X |
| 3,249,070 | 5/1966 | Day et al. ............................. 108/26 |
| 3,339,503 | 9/1967 | Flodell ............................. 108/64 X |
| 4,176,889 | 12/1979 | Gartung ............................ 108/26 X |
| 4,272,136 | 6/1981 | Sengua ................................ 312/196 |
| 4,665,836 | 5/1987 | Burr ..................................... 108/64 |
| 4,732,088 | 3/1988 | Koechlin et al. ..................... 108/64 |

FOREIGN PATENT DOCUMENTS 10595 2/1956 Fed. Rep. of Germany ...... 108/147

Primary Examiner—Joseph Falk
Attorney, Agent, or Firm—Bernard, Rothwell & Brown

[57] ABSTRACT

An operating room instrument table assembly is formed of a plurality of modular table units each having a base frame with castor wheel supports, a table top support frame and a removable table top for positioning instruments, the removable table top being sterilizable as a unit with the instruments. The modular table tops may include receptacles and may be positioned above a drawer. A vertical wall for hanging instruments and a fluorescent light may also be included.

7 Claims, 5 Drawing Sheets

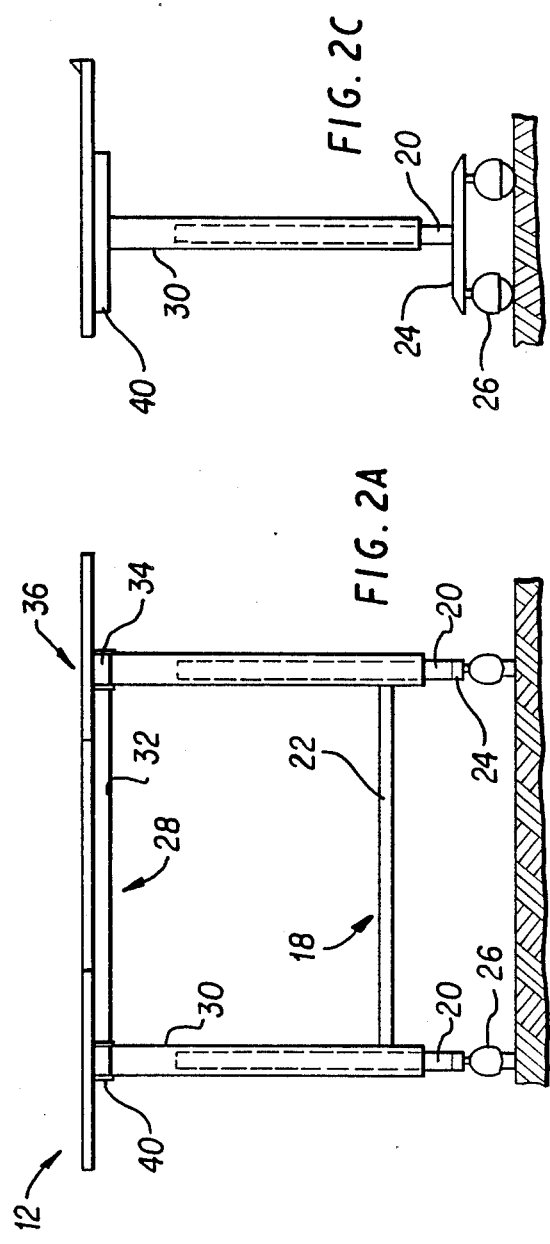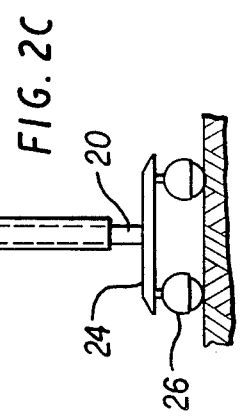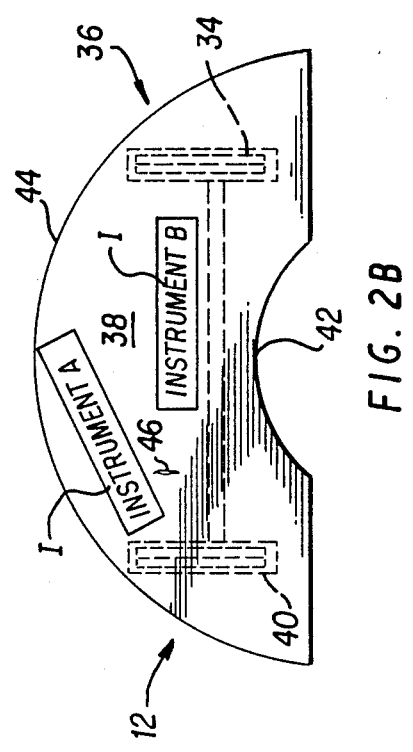

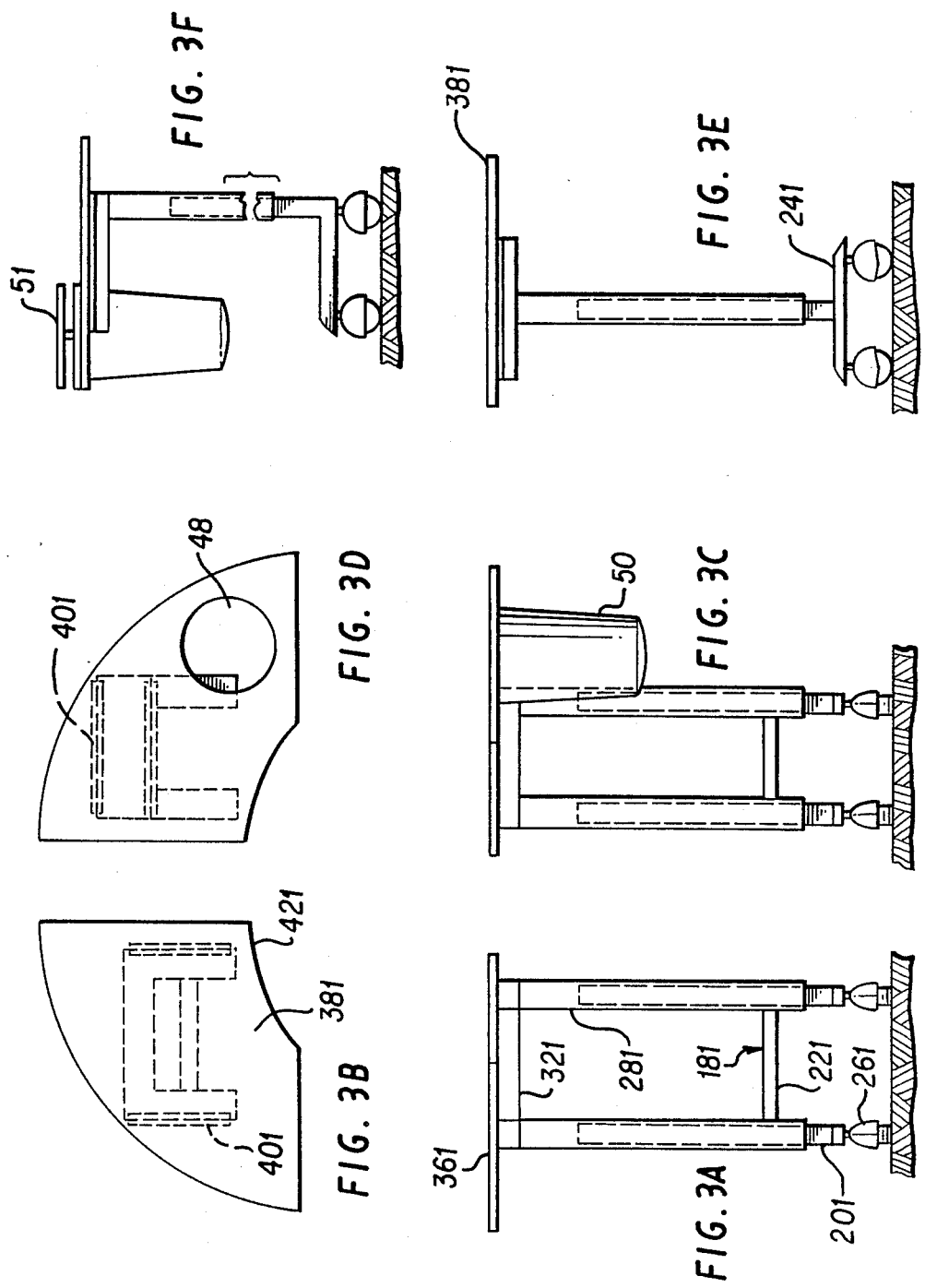

OPERATING ROOM INSTRUMENT TABLE

BACKGROUND OF THE INVENTION

1. Field Of The Invention

This invention relates to improvements in operating room instrument tables and particularly to a modular table of multiple configurations in which instruments can be placed in an orderly fashion and including a portion which can be sterilized with the instruments.

2. Background Art

Operating room instrument tables have changed little over the years. Instrument tables used in operating rooms are tables in which sterile instruments are placed and selected by a scrub nurse and handed to a surgeon conducting the operation. At present the most commonly used tables for holding sterile operating instruments are known as "Mayo" stands (small metal tables) where instruments are thrown resulting in crowding and inefficient handling of the instruments as it takes some time to select them. Typically, the operating instruments are placed on sterile drapes which cover the tables.

There is a significant need in the art to have operating room instrument tables on which instruments can be placed in an orderly fashion depending on the frequency of use, which can be selected depending upon the nurses and surgeons preferences and which can eliminate the need for providing sterile drapes under the instruments which further assists in organizing the instruments for the operation as well as being designed for optimal human interaction in order to minimize errors and fatigue and assure a more efficient handling of the surgical instruments.

SUMMARY OF THE INVENTION

This invention provides an operating room instrument table assembly in which there are a plurality of modular table units specifically configured for use by a nurse. Each of the modular table units includes a wheeled base frame and a removable top portion for holding the surgical instruments. The top portion is attachable to the base so that it may be removed and sterilized as a unit with the instruments and may have a layout or pattern for different instruments in different orders depending upon the operation to be performed.

One or more of the modular table units may have one or more removable drawers below the table top portion for holding further surgical instruments, the drawer and instruments also may be removable as a unit for sterilization and may also have patterns on them for placing the instruments. One or more of the modular tables may further carry receptacles with the receptacle opening at the top of the table. They may also be provided with an upstanding rear wall in the nature of a peg board for hanging and organizing instruments with lighting means at the top of the peg board. The modular units may have a safe stop on the periphery of the table top, may contain the electrical cords required for lighting and may include a removable "lazy susan."

BRIEF DESCRIPTION OF THE DRAWINGS

FIG. 2a is a front elevation view of a U-shaped modular table according to this invention;

FIG. 2b is a top plan view of the table shown in FIG. 2a;

FIG. 2c is a side elevation view of the table shown in FIG. 2a;

FIG. 3a is a front elevation view of a quarter circular modular table according to this invention;

FIG. 3b is a top plan view of the table shown in FIG. 3a;

FIG. 3c is a front elevation view of another form of quarter table;

FIG. 3d is a top plan view of the table shown in FIG. 3c;

FIG. 3e is a side view of the table shown in FIG. 3a;

FIG. 3f is a side view of the FIG. 3c table;

FIG. 4b is a side elevation view of the table shown in FIG. 4a;

FIG. 4c is a top plan view of the table shown in FIG. 4a;

FIG. 5a is a front elevation view of a further form of a modular table according to this invention with removable drawers;

FIG. 5b is a side elevation view of the table shown in FIG. 5a; and

FIG. 5c is a top plan view of the table shown in FIG. 5a.

DETAILED DESCRIPTION OF THE PREFERRED EMBODIMENTS

Figure 1:
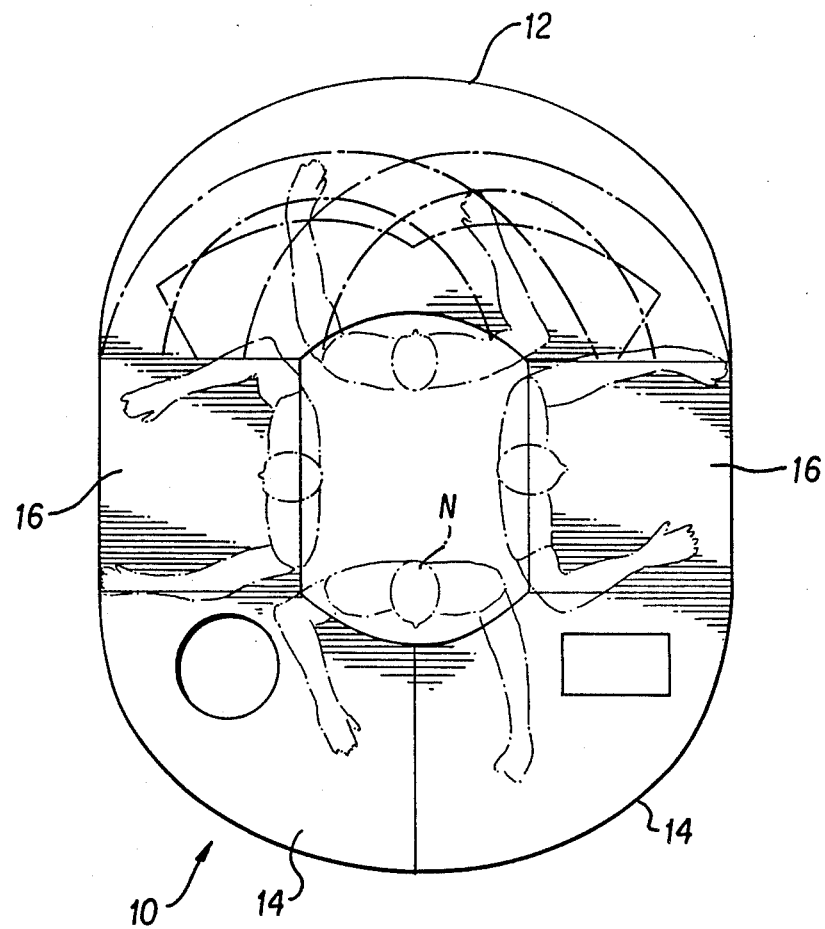
FIG. 1 is a top plan view of an assembly of modular operating room instrument tables according to the present invention showing schematically the position of a scrub nurse.

A modular table assembly of this invention may be constructed of a number of modular units depending upon the scrub nurse or the operating surgeon's preference. As shown in FIG. 1 there is a U-shaped table 12, a pair of quarter circular tables 14 and a pair of rectangular tables 16. Each modular table is configured and sized for optimal human interactions, i.e., an average nurse can reach instruments positioned anywhere on any of the tables.

The U-shaped table 12 is shown in FIGS. 2a, 2b and 2c. It includes a base frame 18 constructed of a pair of posts 20 connected by a connector strut 22. At the bottom of each post there is a foot piece 24 and there is a wheeled castor 26 at each end of the foot piece.

A table top support frame 28 is constructed of tubular supports 30 which fit over the posts 20 and are connected by a center connector 32 and are provided with top head portions 34.

A removable table top member 36 has a top surface portion 38 and railings or sockets 40 for fitting over the members 34 and holding the table top 36 in place but allowing it to be lifted vertically and removed in toto with the surgical operating instruments for sterilization and then replacing.

The table has an indentation 42 at the inner surface so that a nurse may reach any place on the table as shown on FIG. 1 and has a curved outer periphery 44. If desired, indicia I indicating positions of instruments to be placed on the table may be stenciled to indicate the correct placement of the instrument depending upon the particular operation to be performed. See FIG. 2B.

FIGS. 3a, 3b and 3e are views of a quarter circular table similar in concept to the U-shaped table of FIGS. 2a–c in which the reference numerals indicate the same parts with the addition of the digit 1. That is, a base frame 181 supports the table top support frame 281 which carries the table top member 361. The operation and construction is substantially similar except as apparent from review of the drawings. FIGS. 3c, 3d and 3f show another quarter circular table similar to FIGS. 3a, 3b, and 3e except that the table is of an alternate quarter circular configuration, the railing 401' is differently positioned and configured as the table top includes an opening 48 for a receptacle 50 for placing materials previously used in a surgical operation. Alternatively, a removable lazy susan 51 can be removably mounted over opening 48.

Figure 4C:
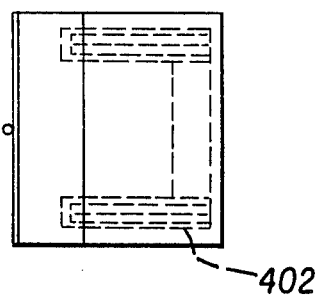
Figure 4A:
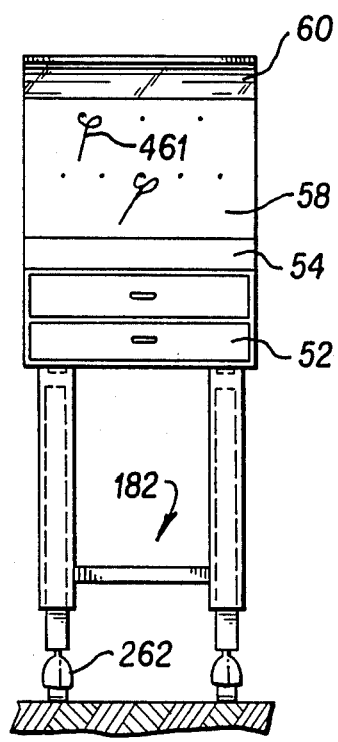
FIG. 4a is a front view of another form of modular table according to this invention.
Figure 4B:
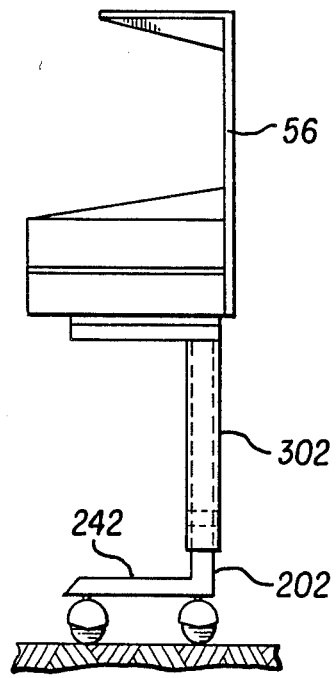

FIGS. 4a, 4b and 4c show a rectangular modular instrument table in which the parts similar to that in FIGS. 2a, 2b and 2c are indicated with the same reference numerals followed by a 2. For example base frame 182 is formed of posts 202 which have feet member 242 with castor-type wheels 262. The entire top assembly includes a plurality of removable drawers 52 which may be individually sterilizable and a removable support surface which again may have indicia for positioning of instruments. A vertical back member 56 has its front surface configured for hanging instruments in the nature of a peg board on which there may be indicia 461 for correctly positioning and hanging the instruments. At the top of back member 56 there is a fluorescent light 60 positioned in an overhang for lighting the surface of the peg board 58 and the surface 54. The drawers 52 may be removed and placed on the surface 54 for easy access to the operating instruments.

Figure 5C:
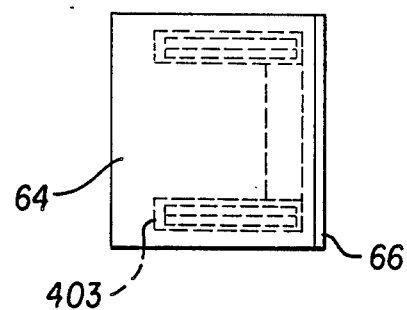
Figures 5A, 5B:
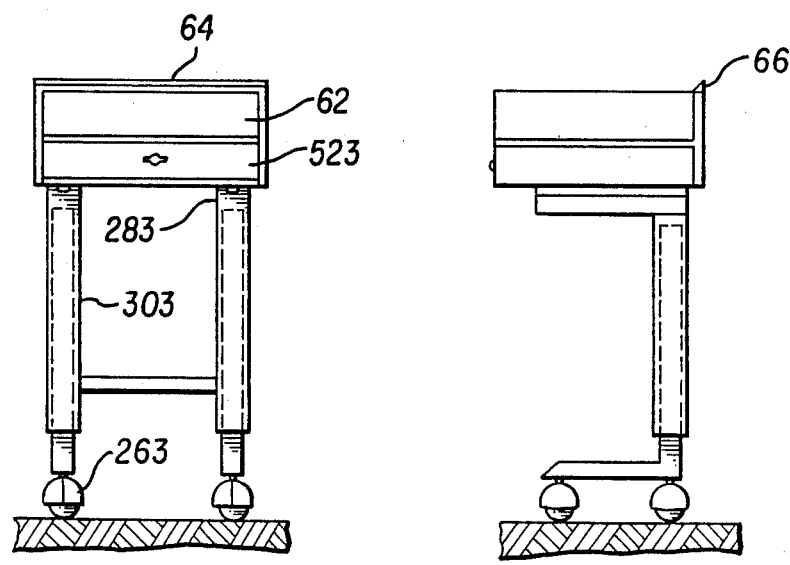

FIGS. 5a, 5b and 5c illustrate another form of modular rectangular table in which reference numerals similar to previously described embodiments are followed by the digit 3. For example, the wheel castors 263 support the table top support frame 283. There is provided a single removable drawer 523 with an open space 62 above it for a fluorescent lamp to light up a table top surface 64 of non-glare glass or the like. A safe stop railing 66 may be positioned along the back of the top as shown.

As can be seen, this invention provides a number of advantages in operating room tables. In particular the modular concept allows for multiple configurations that can be used depending upon the nurses or surgeon's preference. Instruments can be placed in an orderly fashion depending upon the particular operation, the frequency of use and individual preferences, drawers can be provided so that all instruments do not have to be on the top of the table except when needed. The table top and/or drawers can be sterilized with the instruments thus saving substantial amounts of money and drapery. Since the instruments and table top can be sterilized, there is an additional savings in set-up time estimated to be about ½ hour per operating procedure per set-up. Finally, human interaction is optimal and as a result errors are minimized and fatigue is diminished resulting in a more efficient handling of the instruments in a surgical procedure.

What is claimed is:

1. An operating room instrument table assembly, comprising:
   (a) a plurality of modular table units;
   (b) base frame for each of the table units, the base frame having vertical supports, a center connector, feet portions at the bottom of the vertical supports and wheeled castor means depending from the feet portions;
   (c) a table top support frame carried by the base frame, the table top support frame having columns fitting over the base frame supports and having top portions for supporting a table top unit;
   (d) a table top unit having means on the bottom surface thereof for cooperating with the table top support frame to allow the table top unit to be fixedly supported on the support frame and to be removable therefrom;
   (e) a top portion of the table top unit having indicia thereon for the placement of surgical instruments;
   (f) the table top being individually removable and sterilizable as a unit with the instruments.

2. An operating room instrument table as in claim 1 wherein at least one of the modular units has at least one removable drawer below the top portion for holding surgical instruments, the drawer and instruments being removable as a unit for sterilization.

3. An operating room instrument table as defined in claim 1 wherein at least one of the modular table units carries a receptacle with a receptacle opening.

4. An operating room instrument table as defined in claim 1 wherein at least one of the modular table units has a vertical upstanding member at the rear thereof with means thereon for hanging operating instruments.

5. An operating room instrument table as defined in claim 4 wherein the modular table unit with a vertical upstanding member also has lighting means at the top of the vertical member for lighting the surface of the table.

6. An operating room instrument table as defined in claim 1 wherein the top portion of at least one of the modular units has a safe stop on at least a periphery of a top surface thereof.

7. An operating room instrument table as defined in claim 8 wherein at least one of the modular units carries a removable lazy susan.

* * * * *